United States Patent [19]
Gibson et al.

[11] Patent Number: 6,001,967
[45] Date of Patent: Dec. 14, 1999

[54] HERPES VIRUS PROTEINASE AND METHOD OF ASSAYING

[75] Inventors: D. Wade Gibson, Baltimore, Md.; Anthony R. Welch, Sunnyvale, Calif.

[73] Assignee: The Johns Hopkins University, Baltimore, Md.

[21] Appl. No.: 08/251,288

[22] Filed: May 31, 1994

Related U.S. Application Data

[60] Division of application No. 07/798,776, Nov. 27, 1991, Pat. No. 5,434,074, which is a continuation-in-part of application No. 07/725,308, Jul. 5, 1991, abandoned.

[51] Int. Cl.[6] .............................. A61K 38/00; C07K 1/00
[52] U.S. Cl. .......................... 530/345; 530/326; 530/320; 530/327
[58] Field of Search ................................... 530/345, 326, 530/330, 327

[56] References Cited

U.S. PATENT DOCUMENTS

| | | |
|---|---|---|
| 4,772,547 | 9/1988 | Heimer et al. |
| 4,952,674 | 8/1990 | Keller et al. |
| 5,164,300 | 11/1992 | Marshall et al. |

FOREIGN PATENT DOCUMENTS 0 514 830  11/1992  European Pat. Off.

OTHER PUBLICATIONS

Ariyoshi, Y. et al. (1987) Design of sweet peptides based on a sweet receptor model. Pept. Chem. 24, 251–6. see abstract.
Tanaka et al. (1989) *Mol. Cell. Biol.* 9, 757–768. see sequence search report.
Ghiasi, H. et al. (1987) *Virology* 160, 100–109. See sequence search report.
Beinfeld et al., Methods Enzymol. 168, 3–7 (1989). see abstract.
Liu and Roizman, *J. Virol.*, 67(3):1300–1309.
Baum et al., *J. Virol.*, 1993, 67(1):497–506.
Liu and Roizman, *J. Virol.*, 1991 65(1):206–212.
Welch and Gibson, *J. Cell Biochem. Suppl.*, 1991, 15:138.
Gibson et al., *J. Virol.*, 1990, 64(3):1241–1249.
Welch et al., *J. Virol.*, 1991, 65(8):4901–4100.
Welch et al., *Proc. Natl Acad. Sci USA*, 1991, 88:10792–10796.
Liu and Roizman, *J. Virol.*, 1991, 65(10):5149–5156.
Bergmeyer, *Methods In Enzymatic Anaysis*, vol. V, Enzymes 3, 1984, p. 84.
Ohagi et al., *Nucl. Acids. Res.*, 1990, 18(23):7159.
Fling et al., *Mol. Gen. Genet.*, 1991, 227:318–329.
Rich et al., *J. Med. Chem.*, 1990, 33:1285–1288.
Grobelny et al., *Biochem.*, 1989, 28:4948–4951.
Preston et al., *Virology*, 1992, 186:87–98.
Braun et al., *J. Virol.*, 1983, 46(1):103–112.
Braun et al., *J. Virol.*, 1984, 49(1):142–153.
Zweig et al., *J. Virol.*, 1980, 35(3):644–652.
Schenk et al., *J. Virol.*, 1991, 65(3):1525–1529.
Welch et al., *Abstract from 15th International Herpesvirus Workshop*, Aug. 2–8, 1990.

*Primary Examiner*—Anthony C. Caputa
*Assistant Examiner*—Heather A Bakalyor
*Attorney, Agent, or Firm*—Banner & Witcoff, Ltd.

[57] ABSTRACT

A herpes virus proteinase has been found to be encoded by a member of a family of four nested genes in simian cytomegalovirus. Another member of the nested genes encodes the assembly protein precursor, which is a substrate for the proteinase. Homologous genes are found in other herpes viruses. Cleavage sites recognized by the proteinase are identified in cytomegalovirus and are found to be highly conserved in other herpes viruses. Substrates, inhibitors, assay kits, and methods of assaying are provided which rely on the proteinase and its activity.

31 Claims, 7 Drawing Sheets

FIG. IA

```
5'--TTGTCCGACACCCCAGGTTATTGGTGGTCTCCGGGGGGGAACAGGGGGGTTTGCAGG
                    20            40            60

CCTCGGTTAAAGAGAGCAGCACGCAGATGAGTCTCAAGATCTTGAGTTCTTCCAGCCGCAGG
                    80           100           120

GTGTTGAGCGGGCTGTCCCCGCGACATCTTTTCGCTGATCTGTAATATTAGATGATTGGCA
                   140           160           180                EndLeuAla>
                                                                    APNG1→ 240

CAAGTAAAGGAGAATTGCCGGTTCGAACCCGGCCTCCGTGTTGACATGGCCGAT
                   200           220           240
GlnValLysGluAsnLeuProValArgThrArgAlaSerValLeuAspMETAlaAsp>

CCCGTCTACGTCGGGGTTTTTGGTGCGCTACGACGAGCCTCCCGGAGAAGCTGAGCTG
                   260           280           300                      5'End
ProValTyrValGlyGlyPheLeuValAlaArgTyrAspGluProProGlyGluAlaGluLeu>
                                                  320                 360
                                                                    CCGCTGCCCCTG

TTTCTGCCCTCGGGGGTGTAGACCGCTGGTTGCGCGATTGCCGAGGAGCCGAGGCG
                   340           360           380           400
PheLeuProSerGlyValValAlaAspArgTrpLeuArgAspCysArgGlyProLeuProLeu>
                                                              420

AATGTCAATCACGACGAGTCGGCGACCGTGGGCGACCGTATGTGGCTGGGCTCCAGAATGTCCGG
                   420           440           460           480
AsnValAsnHisAspGluSerAlaThrValGlyTyrValAlaGlyLeuGlnAsnValArg>

GCCGGCTTGTTCTGTTTGGGACGTGTTACGTCCCCAAGTTTCTGGATATCGTTCAAAAA
                                   440
AlaGlyLeuPheCysLeuGlyArgValThrSerProLysPheLeuAspIleValGlnLys>
```

FIG. 1B

```
         500            520            540
GCCTCGGAAAAATCCGAGTTGGTGTCCCGGGACCTCCGTCCGAGTCCTCGTTGCGGCCG
AlaSerGluLysSerGluLeuValSerArgGlyProProSerGluSerSerLeuArgPro>
         560            580            600
GACGGGCGTGTTGGAGTTTCTCAGGGGCAGTTATTCGGGGCCTGTCGCCTCTCCAGCCCGA
AspGlyValLeuGluPheLeuSerGlyTyrSerGlyLeuSerLeuSerSerArgArg>
         620            640            660
GATATAAACGCCGGCGATGGCCCGCGCGATGCAGAAACAGCCGTGCTTCAAACATGTG
AspIleAsnAlaAlaAspGlyAlaAlaGlyAspAlaGluThrAlaCysPheLysHisVal>
   TATA                   680            700            720
GCTCTGTGCAGCGTGGGCCCGCCGGGCCACGTTGGCGGTGTATGGCAGGCAGCCAGAT
AlaLeuCysSerValGlyArgArgGlyThrLeuAlaValTyrGlyArgGlnProAsp>
APNG7→    740            760            780
TGGGTGATGGAACGTTTCCCGGATCTCACCGAGGCCGGGAAGGCCTGCGAAATCAG
TrpValMETGluArgPheProAspLeuThrGluAlaAspArgGluAlaLeuArgAsnGln>
         800            820            840
CTATCGGGAAGTGGGGAAGTTGCCGCGAAGGAAAGTGCGGAATCGTCTGCCGCCGCC
LeuSerGlySerGlyGluValAlaAlaAlaLysGluSerAlaGluSerSerAlaAlaAlaAla>
5'Mid         860            880            900
GTCGATCCCTTTCAGTCGGATTCGTACGGGCTGTTGGGAACAGTGTGGACGCGCTGTAC
ValAspProPheGlnSerAspSerTyrGlyLeuLeuGlyLeuAsnSerValAspAlaLeuTyr>
         920            940            960
ATTCAAGAGCGTCTCCCTAAGCTGCCTATGACAAGCCGGTCGGGGTCACGGCTCGG
IleGlnGluArgLeuProLysLeuProMETThrSerArgLeuValGlyValThrAlaArg>
         980           1000           1020
GAGTCGTACGTGAAAGCCAGTGTTTCGCCCGACCAGGAGACGTGCGATATTAAAGTA
GluSerTyrValLysAlaSerValSerProAlaGluGlnGluThrCysAspIleLysVal>
                                              TATAAAGTA
```

FIG. IC

```
         1040                  1060        APNG.5→1080
GAAAAAGAGCGGCCGAAGGAGCCAGAGCAGAGAGCCACGTACCGACCGAGTCAATGTCTCAC
GluLysGluArgProLysGluProGluGlnSerHisValProThrGluSerMETSerHis>
                    1100                  1120                  1140
CCTATGAGCGCCGTGGCTACTCCGGCTACAGCCTCGACGCCGTCGCGCCTTCTCAGGCGCTG
ProMetSerAlaValAlaThrProAlaAlaSerThrValAlaProSerGlnAlaProLeu>
                    1160    3'Mid          1180                  1200
GCGCTGGCCCATGACGGTGTTATTACCTAAAGACGCTTTTTCTCGCTCATCGGGGCC
AlaLeuAlaHisAspGlyValTyrLeuProLysAspAlaPhePheSerLeuIleGlyAla>
                    1220                  1240                  1260
AGTCGTCCCCTGGCCGAGGCGGGAGCCGGCGTATCCGGCTGTCCCGCCGCCA
SerArgProLeuAlaGluAlaAlaGlyAlaAlaArgAlaAlaTyrProAlaValProProPro>
                    1280                  1300                  1320
CCCGCGTATCCGGTAATGAATTATGAGGACCCCTCCTCACGTCACTTTGACTACAGTGCC
ProAlaTyrProValMETAsnTyrGluAspProSerSerArgHisPheAspTyrSerAla>
                    1340                  1360                  1380
TGGCTGCGGCGGCCAGCTTATGACGCTTATGCCGACGCCCGTGCCCTCCTCCCCGTCATGCCC
TrpLeuArgArgProAlaTyrAspAlaTyrAlaAspAlaProLeuProProProProValMetPro>
                    1400                  1420                  1440
ATGCCGTATCGCAGACGCGACCCCATGATGGAGGAGGCCGAGGCCGCCTGGGAGCGC
MetProTyrArgArgArgAspProMetMetGluGluAlaGluAlaArgAlaAlaTrpGluArg>
                    1460                  1480                  1500
GGGTACGCCTTCTGCTTATGACCACTACGTGAACAACGGCTCCTGGTCGCGGAGCCGC
GlyTyrAlaProSerAlaTyrAspHisTyrValAlaAsnGlySerTrpSerArgSerArg>
```

FIG. ID

```
                  1520                   1540                   1560
AGCGGCGGCTCAAGAGGAGGAGGCGGACGCGTCCTCGGATGAGGAAGAGGACATG
 SerGlyAlaLeuLysArgArgGluArgAspAlaSerSerAspGluGluAspMet>
                  1580                   1600                   1620
AGTTTCCCGGGAAGCCGACCACGGCAAGGCTCGGAAAAGACTCAAAGCTCATCACGGG
 SerPheProGlyGluAlaAspHisGlyLysAlaArgLeuLysArgLeuLysAlaHisHisGly>
                  1640                   1660                   1680
CGTGATAATAACAACTCTGGGAGCCGATGCCAAGGGCGATCGGTACGACGACATTCGGAA
 ArgAspAsnAsnSerGlySerAspAlaLysGlyAspArgTyrAspAspIleArgGlu>
                  1700                   1720                   1740
GCGTTACAGGAGCTGAAGCGCGAGATGCTGGCCGTGCGCAGATCGCGCCACGTGCGCTC
 AlaLeuGlnGluLeuLysArgGluMetLeuAlaValArgGlnIleAlaProArgAlaLeu>
                  1760                   1780                   1800
TTGGCCCCGCACAGTCAGCGCTAGCGACGCCCGTGGCTTCTCCGACAACGACCACGTCGCATCAA
 LeuAlaProAlaThrProValAlaSerProThrThrThrSerProSerHisGln>
                  1820                   1840                   1860
GCCGAGGCTAGCGAACCTCAGGACGCATCGACTGCCGCCGTCAACCGCTTCG
 AlaGluAlaSerGluProGlnAlaSerThrAlaAlaAlaAlaSerProSerThrAlaSer>
                  1880                   1900                   1920
TCGCACGGCAGCAAGTCGGCGAACGCGGGTGGTGAACGCGCTCGTGTCGCCGTTGCGCCT
 SerHisGlySerLysSerAlaGluArgGlyValValAsnAlaSerCysArgValAlaPro>
                  1940                   1960                   1980
CCGTTGGAGGCTGTGAACCCCCTAAGGACATGGTGGACTTGAATCGTCGCCTGTTGTG
 ProLeuGluAlaValAsnProProLysAspMetValAspLeuAsnArgArgLeuPheVal>
                  2000
GCGGCGTTGAATAAAATGGAATAAAAACTCGTAC-3'
 AlaAlaLeuAsnLysMetGluEnd
```

FIG. 2

| HERPESVIRUS | CONSERVED REGION | |
|---|---|---|
| SIMIAN CMV (COLBURN) | PLPLNVNHDESATVGYV | FKHVALCSVGRRRGTLAVYG |
| HUMAN CMV (AD169) | ALPLNI NHDDTAVVGHV | FKHVALCSVGRRRGTLAVYG |
| HSV-1 | PLPINVDHRAGCEVGRV | FAHVALCA I GRR LGT IVTYD |
| VZV | KI PI NI DHRKDCVVGEV | FTHVALCVVGRRVGTVVNYD |
| EBV | PLPLTVEH LPDAPVGSV | FDHVSI CALGRRRGTTAVYG |
| ILTV | TI PI NI DH ESSCVVGTV | FAHVALCELGRREGTVAI YG |
| | CONSERVED MOTIF 2 | CONSERVED MOTIF 1 |

FIG. 3A

| VIRUS | RECOGNITION/CLEAVAGE DOMAIN |
|---|---|
| SCMV | SKSAERGVVNA ↓ SCRVAPP |
| HCMV | AERAQAGVVNA ↓ SCRLATA |
| HSV-1 | SNAEAG ALVNA ↓ SSAAHVD |
| VZV | HTDTVGQDVNA ↓ VEASSKA |
| EBV | GHHRGKKLVQA ↓ SASGVAQ |
| ILTV | NQESARETVDA ↓ SMPKRLK |
| HHV-6 | AA SPKPS I LNA ↓ S - - - - - |

FIG. 3B

| | |
|---|---|
| COLBURN: | VTARESYVKA ↓ SVSPAEQETC |
| HCMV AD169: | VTERESYVKA ↓ SVSPEARAI L |
| HSV-1: | GIAGHTYLQA ↓ SEKFKMWGAE |
| VZV: | GIMGHVYLQA ↓ STGYGLAR I T |
| EBV: | NI PAESYLK A ↓ SDAPDLQKPD |
| ILTV: | AVYNPKYLQA ↓ NEVI TI GI K E |

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
      (A) LENGTH: 2014 base pairs
      (B) TYPE: nucleic acid
      (C) STRANDEDNESS: single
      (D) TOPOLOGY: linear (xi) SEQUENCE DESCRIPTION: SEQ ID NO:1:

```
TTGTCCGACA CCCCCAGGTT ATTGGTGGTC TCGCGGGGGG GGAACAGGGG GGTTTGCAGG        60

CCTCGGTTAA AGAGCAGCAC GCAGATGAGT CTCAAGATCT TGAGTTCTTC CAGCCGCAGG       120

GTGTTGAGCG GCTGTCCCCG CGACATCTTT TCGCTGATCT GTAATATTAG ATGATTGGCA       180
```

```
CAAGTAAAGG AGAATTTGCC GGTTCGAACC CGGGCCTCCT CCGTGTTGGA CATGGCCGAT    240

CCCGTCTACG TCGGGGGTTT TTTGGTGCGC TACGACGAGC CTCCCGGAGA AGCTGAGCTG    300

TTTCTGCCCT CGGGGGTGGT AGACCGCTGG TTGCGCGATT GCCGAGGCCC GCTGCCCCTG    360

AATGTCAATC ACGACGAGTC GGCGACCGTG GGCTATGTGG CTGGGCTCCA GAATGTCCGG    420

GCCGGCTTGT TCTGTTTGGG ACGTGTTACG TCCCCCAAGT TTCTGGATAT CGTTCAAAAA    480

GCCTCGGAAA AATCCGAGTT GGTGTCCCGG GGACCTCCGT CCGAGTCCTC GTTGCGGCCG    540

GACGGCGTGT TGGAGTTTCT CAGCGGCAGT TATTCGGGCC TGTCGCTCTC CAGCCGCCGA    600

GATATAAACG CGGCCGATGG CGCCGCGGGC GATGCAGAAA CAGCGTGCTT CAAACATGTG    660

GCTCTGTGCA GCGTGGGCCG CCGCCGGGGC ACGTTGGCGG TGTATGGCAG GCAGCCAGAT    720

TGGGTGATGG AACGTTTCCC GGATCTCACC GAGGCCGACC GGGAAGCGCT GCGAAATCAG    780

CTATCGGGAA GTGGGAAGT TGCCGCGAAG GAAAGTGCGG AATCGTCTGC CGCCGCCGCC    840

GTCGATCCCT TTCAGTCGGA TTCGTACGGG CTGTTGGGGA ACAGTGTGGA CGCGCTGTAC    900

ATTCAAGAGC GTCTCCCTAA GCTGCGCTAT GACAAGCGGC TGGTCGGGGT CACGGCTCGG    960

GAGTCGTACG TGAAAGCCAG TGTTTCGCCC GCCGAGCAGG AGACGTGCGA TATTAAAGTA   1020

GAAAAAGAGC GGCCGAAGGA GCCAGAGCAG AGCCACGTAC CGACCGAGTC AATGTCTCAC   1080

CCTATGAGCG CCGTGGCTAC TCCGGCGGCC TCGACCGTCG CGCCTTCTCA GGCGCCGCTG   1140

GCGCTGGCCC ATGACGGTGT TTATTTACCT AAAGACGCTT TTTTCTCGCT CATCGGGGCC   1200

AGTCGTCCCC TGGCCGAGGC GGCGGGAGCG CGCGCCGCGT ATCCGGCTGT CCCGCCGCCA   1260

CCCGCGTATC CGGTAATGAA TTATGAGGAC CCCTCCTCAC GTCACTTTGA CTACAGTGCC   1320

TGGCTGCGGC GGCCAGCTTA TGACGCCGTG CCTCCCCTGC CTCCTCCCCC CGTCATGCCC   1380

ATGCCGTATC GCAGACGCGA CCCCATGATG GAGGAGGCCG AGCGCGCCGC CTGGGAGCGC   1440

GGGTACGCGC CTTCTGCTTA TGACCACTAC GTGAACAACG GCTCCTGGTC GCGGAGCCGC   1500

AGCGGCGCGC TCAAGAGGCG AAGGGAGCGC GACGCGTCCT CGGATGAGGA AGAGGACATG   1560

AGTTTTCCCG GGGAAGCCGA CCACGGCAAG GCTCGGAAAA GACTCAAAGC TCATCACGGG   1620

CGTGATAATA ACAACTCTGG GAGCGATGCC AAGGGCGATC GGTACGACGA CATTCGGGAA   1680

GCGTTACAGG AGCTGAAGCG CGAGATGCTG GCCGTGCGGC AGATCGCGCC ACGTGCGCTC   1740

TTGGCCCCCG CACAGCTAGC GACGCCCGTG GCTTCTCCGA CAACGACCAC GTCGCATCAA   1800

GCCGAGGCTA GCGAACCTCA GGCATCGACT GCCGCTGCCG CGTCGCCGTC AACCGCTTCG   1860

TCGCACGGCA GCAAGTCGGC CGAACGCGGG GTGGTGAACG CCTCGTGTCG CGTTGCGCCT   1920

CCGTTGGAGG CTGTGAACCC CCCTAAGGAC ATGGTGGACT TGAATCGTCG CCTGTTTGTG   1980

GCGGCGTTGA ATAAAATGGA ATAAAAACTC GTAC                              2014
```

(2) INFORMATION FOR SEQ ID NO:2:

(i) SEQUENCE CHARACTERISTICS:
        (A) LENGTH: 609 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

```
Leu Ala Gln Val Lys Glu Asn Leu Pro Val Arg Thr Arg Ala Ser Ser
 1               5                  10                  15

Val Leu Asp Met Ala Asp Pro Val Tyr Val Gly Gly Phe Leu Val Arg
```

-continued

```
                20                  25                  30
Tyr Asp Glu Pro Pro Gly Glu Ala Glu Leu Phe Leu Pro Ser Gly Val
            35                  40                  45
Val Asp Arg Trp Leu Arg Asp Cys Arg Gly Pro Leu Pro Leu Asn Val
 50                  55                  60
Asn His Asp Glu Ser Ala Thr Val Gly Tyr Val Ala Gly Leu Gln Asn
 65                  70                  75                  80
Val Arg Ala Gly Leu Phe Cys Leu Gly Arg Val Thr Ser Pro Lys Phe
                85                  90                  95
Leu Asp Ile Val Gln Lys Ala Ser Glu Lys Ser Glu Leu Val Ser Arg
                100                 105                 110
Gly Pro Pro Ser Glu Ser Ser Leu Arg Pro Asp Gly Val Leu Glu Phe
                115                 120                 125
Leu Ser Gly Ser Tyr Ser Gly Leu Ser Leu Ser Arg Arg Asp Ile
 130                 135                 140
Asn Ala Ala Asp Gly Ala Ala Gly Asp Ala Glu Thr Ala Cys Phe Lys
 145                 150                 155                 160
His Val Ala Leu Cys Ser Val Gly Arg Arg Gly Thr Leu Ala Val
                165                 170                 175
Tyr Gly Arg Gln Pro Asp Trp Val Met Glu Arg Phe Pro Asp Leu Thr
                180                 185                 190
Glu Ala Asp Arg Glu Ala Leu Arg Asn Gln Leu Ser Gly Ser Gly Glu
                195                 200                 205
Val Ala Ala Lys Glu Ser Ala Glu Ser Ser Ala Ala Ala Val Asp
 210                 215                 220
Pro Phe Gln Ser Asp Ser Tyr Gly Leu Leu Gly Asn Ser Val Asp Ala
 225                 230                 235                 240
Leu Tyr Ile Gln Glu Arg Leu Pro Lys Leu Arg Tyr Asp Lys Arg Leu
                245                 250                 255
Val Gly Val Thr Ala Arg Glu Ser Tyr Val Lys Ala Ser Val Ser Pro
                260                 265                 270
Ala Glu Gln Glu Thr Cys Asp Ile Lys Val Glu Lys Glu Arg Pro Lys
                275                 280                 285
Glu Pro Glu Gln Ser His Val Pro Thr Glu Ser Met Ser His Pro Met
                290                 295                 300
Ser Ala Val Ala Thr Pro Ala Ala Ser Thr Val Ala Pro Ser Gln Ala
 305                 310                 315                 320
Pro Leu Ala Leu Ala His Asp Gly Val Tyr Leu Pro Lys Asp Ala Phe
                325                 330                 335
Phe Ser Leu Ile Gly Ala Ser Arg Pro Leu Ala Glu Ala Ala Gly Ala
                340                 345                 350
Arg Ala Ala Tyr Pro Ala Val Pro Pro Pro Ala Tyr Pro Val Met
                355                 360                 365
Asn Tyr Glu Asp Pro Ser Ser Arg His Phe Asp Tyr Ser Ala Trp Leu
 370                 375                 380
Arg Arg Pro Ala Tyr Asp Ala Val Pro Pro Leu Pro Pro Pro Val
 385                 390                 395                 400
Met Pro Met Pro Tyr Arg Arg Asp Pro Met Met Glu Glu Ala Glu
                405                 410                 415
Arg Ala Ala Trp Glu Arg Gly Tyr Ala Pro Ser Ala Tyr Asp His Tyr
                420                 425                 430
Val Asn Asn Gly Ser Trp Ser Arg Ser Arg Ser Gly Ala Leu Lys Arg
                435                 440                 445
```

```
Arg Arg Glu Arg Asp Ala Ser Ser Asp Glu Glu Asp Met Ser Phe
    450             455             460
Pro Gly Glu Ala Asp His Gly Lys Ala Arg Lys Arg Leu Lys Ala His
465                 470             475              480
His Gly Arg Asp Asn Asn Asn Ser Gly Ser Asp Ala Lys Gly Asp Arg
                485             490              495
Tyr Asp Asp Ile Arg Glu Ala Leu Gln Glu Leu Lys Arg Glu Met Leu
            500             505             510
Ala Val Arg Gln Ile Ala Pro Arg Ala Leu Leu Ala Pro Ala Gln Leu
        515             520             525
Ala Thr Pro Val Ala Ser Pro Thr Thr Thr Ser His Gln Ala Glu
    530             535             540
Ala Ser Glu Pro Gln Ala Ser Thr Ala Ala Ala Ser Pro Ser Thr
545             550             555             560
Ala Ser Ser His Gly Ser Lys Ser Ala Glu Arg Gly Val Val Asn Ala
                565             570             575
Ser Cys Arg Val Ala Pro Pro Leu Glu Ala Val Asn Pro Pro Lys Asp
            580             585             590
Met Val Asp Leu Asn Arg Arg Leu Phe Val Ala Ala Leu Asn Lys Met
        595             600             605
Glu (2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

Ser Lys Ser Ala Glu Arg Gly Val Val Asn Ala Ser Cys Arg Val Ala
1               5                   10                  15
Pro Pro (2) INFORMATION FOR SEQ ID NO:4:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

Ala Glu Arg Ala Gln Ala Gly Val Val Asn Ala Ser Cys Arg Leu Ala
1               5                   10                  15
Thr Ala (2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:
```

```
Ser Asn Ala Glu Ala Gly Ala Leu Val Asn Ser Ser Ala Ala His
 1               5                  10                  15

Val Asp
```

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

```
His Thr Asp Thr Val Gly Gln Asp Val Asn Ala Val Glu Ala Ser Ser
 1               5                  10                  15

Lys Ala
```

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:7:

```
Gly His His Arg Gly Lys Lys Leu Val Gln Ala Ser Ala Ser Gly Val
 1               5                  10                  15

Ala Gln
```

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

```
Asn Gln Glu Ser Ala Arg Glu Thr Val Asp Ala Ser Met Pro Lys Arg
 1               5                  10                  15

Leu Lys
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

```
Ala Ala Ser Pro Lys Pro Ser Ile Leu Asn Ala Ser
 1               5                  10
```

(2) INFORMATION FOR SEQ ID NO:10:

(i) SEQUENCE CHARACTERISTICS:

(A) LENGTH: 20 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:10:

Val Thr Ala Arg Glu Ser Tyr Val Lys Ala Ser Val Ser Pro Ala Glu
 1               5                  10                  15

Gln Glu Thr Cys
         20

(2) INFORMATION FOR SEQ ID NO:11:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:11:

Val Thr Glu Arg Glu Ser Tyr Val Lys Ala Ser Val Ser Pro Glu Ala
 1               5                  10                  15

Arg Ala Ile Leu
         20

(2) INFORMATION FOR SEQ ID NO:12:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:12:

Gly Ile Ala Gly His Thr Tyr Leu Gln Ala Ser Glu Lys Phe Lys Met
 1               5                  10                  15

Trp Gly Ala Glu
         20

(2) INFORMATION FOR SEQ ID NO:13:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:13:

Gly Ile Met Gly His Val Tyr Leu Gln Ala Ser Thr Gly Tyr Gly Leu
 1               5                  10                  15

Ala Arg Ile Thr
         20

(2) INFORMATION FOR SEQ ID NO:14:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:14:

Asn Ile Pro Ala Glu Ser Tyr Leu Lys Ala Ser Asp Ala Pro Asp Leu
 1               5                  10                  15

Gln Lys Pro Asp
            20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

Ala Val Tyr Asn Pro Lys Tyr Leu Gln Ala Asn Glu Val Ile Thr Ile
 1               5                  10                  15

Gly Ile Lys Glu
            20

(2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

Pro Leu Pro Leu Asn Val Asn His Asp Glu Ser Ala Thr Val Gly Tyr
 1               5                  10                  15

Val (2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

Phe Lys His Val Ala Leu Cys Ser Val Gly Arg Arg Arg Gly Thr Leu
 1               5                  10                  15

Ala Val Tyr Gly
            20

(2) INFORMATION FOR SEQ ID NO:18:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

```
Ala Leu Pro Leu Asn Ile Asn His Asp Asp Thr Ala Val Val Gly His
1               5                   10                  15
Val
```

(2) INFORMATION FOR SEQ ID NO:19:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

```
Phe Lys His Val Ala Leu Cys Ser Val Gly Arg Arg Arg Gly Thr Leu
1               5                   10                  15
Ala Val Tyr Gly
            20
```

(2) INFORMATION FOR SEQ ID NO:20:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:20:

```
Pro Leu Pro Ile Asn Val Asp His Arg Ala Gly Cys Glu Val Gly Arg
1               5                   10                  15
Val
```

(2) INFORMATION FOR SEQ ID NO:21:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:21:

```
Phe Ala His Val Ala Leu Cys Ala Ile Gly Arg Arg Leu Gly Thr Ile
1               5                   10                  15
Val Thr Tyr Asp
            20
```

(2) INFORMATION FOR SEQ ID NO:22:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:22:

```
Lys Ile Pro Ile Asn Ile Asp His Arg Lys Asp Cys Val Val Gly Glu
1               5                   10                  15
Val
```

-continued (2) INFORMATION FOR SEQ ID NO:23:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:23:

Phe Thr His Val Ala Leu Cys Val Val Gly Arg Arg Val Gly Thr Val
 1               5                  10                  15

Val Asn Tyr Asp
            20

(2) INFORMATION FOR SEQ ID NO:24:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

Pro Leu Pro Leu Thr Val Glu His Leu Pro Asp Ala Pro Val Gly Ser
 1               5                  10                  15

Val (2) INFORMATION FOR SEQ ID NO:25:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:25:

Phe Asp His Val Ser Ile Cys Ala Leu Gly Arg Arg Arg Gly Thr Thr
 1               5                  10                  15

Ala Val Tyr Gly
            20

(2) INFORMATION FOR SEQ ID NO:26:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

Thr Ile Pro Ile Asn Ile Asp His Glu Ser Ser Cys Val Val Gly Thr
 1               5                  10                  15

Val (2) INFORMATION FOR SEQ ID NO:27:

(i) SEQUENCE CHARACTERISTICS:
        (A) LENGTH: 20 amino acids
        (B) TYPE: amino acid
        (C) STRANDEDNESS: single (D) TOPOLOGY: linear (ii) MOLECULE TYPE: None (xi) SEQUENCE DESCRIPTION: SEQ ID NO:27:

Phe Ala His Val Ala Leu Cys Glu Leu Gly Arg Arg Glu Gly Thr Val
 1               5                  10                  15

Ala Ile Tyr Gly
            20

(2) INFORMATION FOR SEQ ID NO:28:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: None
            (B) LOCATION: 1...1
            (D) OTHER INFORMATION:  leu
            (A) NAME/KEY: Other
            (B) LOCATION: 2...2
            (D) OTHER INFORMATION: gly, ser, thr, cys, tyr, asn, gln, asp,
                lys, arg, glu, or
            (A) NAME/KEY: Other
            (B) LOCATION: 4...4
            (D) OTHER INFORMATION: ser, val, or asn (xi) SEQUENCE DESCRIPTION: SEQ ID NO:28:

Xaa Xaa Ala Xaa
 1

(2) INFORMATION FOR SEQ ID NO:29:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...1
            (D) OTHER INFORMATION: val or leu
            (A) NAME/KEY: Other
            (B) LOCATION: 2...2
            (D) OTHER INFORMATION: gly, ser, thr, cys, tyr, asn, gln, asp,
                lys, arg, or his
            (A) NAME/KEY: Other
            (B) LOCATION: 4...4
            (D) OTHER INFORMATION: ser, val, or asn (xi) SEQUENCE DESCRIPTION: SEQ ID NO:29:

Xaa Xaa Ala Xaa
 1

(2) INFORMATION FOR SEQ ID NO:30:

(i) SEQUENCE CHARACTERISTICS:
            (A) LENGTH: 4 amino acids
            (B) TYPE: amino acid
            (C) STRANDEDNESS: single
            (D) TOPOLOGY: linear (ix) FEATURE:
            (A) NAME/KEY: Other
            (B) LOCATION: 1...1

```
            (D) OTHER INFORMATION: val or leu
            (A) NAME/KEY: Other
            (B) LOCATION: 2...2
            (D) OTHER INFORMATION: gly, ser, thr, cys, tyr, asn, gln, asp,
                  lys, arg, glu, or
            (A) NAME/KEY: Other
            (B) LOCATION: 4...4
            (D) OTHER INFORMATION: ser or asn (xi) SEQUENCE DESCRIPTION: SEQ ID NO:30:

Xaa Xaa Ala Xaa
1

(2) INFORMATION FOR SEQ ID NO:31:

(i) SEQUENCE CHARACTERISTICS:
            (A) LENGTH: 4 amino acids
            (B) TYPE: amino acid
            (C) STRANDEDNESS: single
            (D) TOPOLOGY: linear (ix) FEATURE:
            (A) NAME/KEY: None
            (B) LOCATION: 1...1
            (D) OTHER INFORMATION: val or leu
            (A) NAME/KEY: Other
            (B) LOCATION: 2...2
            (D) OTHER INFORMATION: gly, ser, thr, cys, tyr, asn, gln, asp,
                  glu, lys, arg, or
            (A) NAME/KEY: Other
            (B) LOCATION: 4...4
            (D) OTHER INFORMATION: ser, val, or asn (xi) SEQUENCE DESCRIPTION: SEQ ID NO:31:

Xaa Xaa Ala Xaa
1

(2) INFORMATION FOR SEQ ID NO:32:

(i) SEQUENCE CHARACTERISTICS:
            (A) LENGTH: 5 amino acids
            (B) TYPE: amino acid
            (C) STRANDEDNESS: single
            (D) TOPOLOGY: linear (ix) FEATURE:
            (A) NAME/KEY: Other
            (B) LOCATION: 2...2
            (D) OTHER INFORMATION: val or leu
            (A) NAME/KEY: Other
            (B) LOCATION: 3...3
            (D) OTHER INFORMATION: lys or gln
            (A) NAME/KEY: Other
            (B) LOCATION: 5...5
            (D) OTHER INFORMATION: ser or asn (xi) SEQUENCE DESCRIPTION: SEQ ID NO:32:

Tyr Xaa Xaa Ala Xaa
1               5

(2) INFORMATION FOR SEQ ID NO:33:

(i) SEQUENCE CHARACTERISTICS:
            (A) LENGTH: 5 amino acids
            (B) TYPE: amino acid
            (C) STRANDEDNESS: single
            (D) TOPOLOGY: linear (ix) FEATURE:
            (A) NAME/KEY: Other
            (B) LOCATION: 2...2
            (D) OTHER INFORMATION: val or leu
            (A) NAME/KEY: Other
            (B) LOCATION: 3...3
```

(D) OTHER INFORMATION:  lys or gln
            (A) NAME/KEY: Other
            (B) LOCATION: 5...5
            (D) OTHER INFORMATION: ser or asn (xi) SEQUENCE DESCRIPTION: SEQ ID NO:33:

Tyr Xaa Xaa Ala Xaa
1               5

(2) INFORMATION FOR SEQ ID NO:34:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
            (A) NAME/KEY: Other
            (B) LOCATION: 1...1
            (D) OTHER INFORMATION:  val or leu
            (A) NAME/KEY: Other
            (B) LOCATION: 2...2
            (D) OTHER INFORMATION:  gly, ser, thr, cys, tyr, asn, gln, asp,
                glu, lys, arg, o
            (A) NAME/KEY: Other
            (B) LOCATION: 4...4
            (D) OTHER INFORMATION:  ser, val, or asn (xi) SEQUENCE DESCRIPTION: SEQ ID NO:34:

Xaa Xaa Ala Xaa
1

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
            (A) NAME/KEY: Other
            (B) LOCATION: 2...2
            (D) OTHER INFORMATION:  val or leu
            (A) NAME/KEY: Other
            (B) LOCATION: 3...3
            (D) OTHER INFORMATION:  lys or gln
            (A) NAME/KEY: Other
            (B) LOCATION: 5...5
            (D) OTHER INFORMATION:  ser or asn (xi) SEQUENCE DESCRIPTION: SEQ ID NO:35:

Tyr Xaa Xaa Ala Xaa
1               5

(2) INFORMATION FOR SEQ ID NO:36:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
            (A) NAME/KEY: Other
            (B) LOCATION: 1...1
            (D) OTHER INFORMATION: leu
            (A) NAME/KEY: Other
            (B) LOCATION: 2...2
            (D) OTHER INFORMATION: gly, ser, thr, cys, tyr, asn, gln, asp,
                glu, lys, arg, or
            (A) NAME/KEY: Other
            (B) LOCATION: 4...4

(D) OTHER INFORMATION:  ser, val, or asn (xi) SEQUENCE DESCRIPTION: SEQ ID NO:36:

Xaa Xaa Ala Xaa
 1

(2) INFORMATION FOR SEQ ID NO:37:

(i) SEQUENCE CHARACTERISTICS:
         (A) LENGTH: 4 amino acids
         (B) TYPE: amino acid
         (C) STRANDEDNESS: single
         (D) TOPOLOGY: linear (ix) FEATURE:
         (A) NAME/KEY: Other
         (B) LOCATION: 1...1
         (D) OTHER INFORMATION:   val or leu
         (A) NAME/KEY: Other
         (B) LOCATION: 2...2
         (D) OTHER INFORMATION:   gly, ser, thr, cys, tyr, asn, gln,
             asp, lys, arg, or hi
         (A) NAME/KEY: Other
         (B) LOCATION: 4...4
         (D) OTHER INFORMATION:  ser, val, or asn (xi) SEQUENCE DESCRIPTION: SEQ ID NO:37:

Xaa Xaa Ala Xaa
 1

(2) INFORMATION FOR SEQ ID NO:38:

(i) SEQUENCE CHARACTERISTICS:
         (A) LENGTH: 4 amino acids
         (B) TYPE: amino acid
         (C) STRANDEDNESS: single
         (D) TOPOLOGY: linear (ix) FEATURE:
         (A) NAME/KEY: Other
         (B) LOCATION: 1...1
         (D) OTHER INFORMATION: val or leu
         (A) NAME/KEY: Other
         (B) LOCATION: 2...2
         (D) OTHER INFORMATION:    gly, ser, thr, cys, tyr, asn, gln,
             asp, lys, arg, glu
         (A) NAME/KEY: Other
         (B) LOCATION: 4...4
         (D) OTHER INFORMATION:  ser or asn (xi) SEQUENCE DESCRIPTION: SEQ ID NO:38:

Xaa Xaa Ala Xaa
 1

(2) INFORMATION FOR SEQ ID NO:39:

(i) SEQUENCE CHARACTERISTICS:
         (A) LENGTH: 5 amino acids
         (B) TYPE: amino acid
         (C) STRANDEDNESS: single
         (D) TOPOLOGY: linear (ix) FEATURE:
         (A) NAME/KEY: Other
         (B) LOCATION: 2...2
         (D) OTHER INFORMATION: val or leu
         (A) NAME/KEY: Other
         (B) LOCATION: 3...3
         (D) OTHER INFORMATION:  lys or gln
         (A) NAME/KEY: Other
         (B) LOCATION: 5...5
         (D) OTHER INFORMATION: ser or asn -continued (xi) SEQUENCE DESCRIPTION: SEQ ID NO:39:

Tyr Xaa Xaa Ala Xaa
1               5

HERPES VIRUS PROTEINASE AND METHOD OF ASSAYING

This application is a division of application Ser. No. 07/798,776 now U.S. Pat. No. 5,434,074, filed Nov. 27, 1991; which is a continuation-in-part of application Ser. No. 07/725,308, filed on Jul. 5, 1991, now abandoned.

This invention was supported under NIH Research Grants RO1 AI22711 and RO1 AI13718. The United States Government retains certain rights in this invention.

TECHNICAL AREA OF THE INVENTION

This invention relates to the area of herpes virology. More particularly, it relates to a new enzyme and the use of that enzyme as a target for anti-viral therapy.

BACKGROUND OF THE INVENTION

Herpes viruses are large double stranded DNA viruses that are responsible for a number of human diseases including chicken pox, shingles, fever blisters, salivary gland virus disease, and infectious mononucleosis. The seven human herpes viruses that have been described thus far are HSV-1, HSV-2, cytomegalovirus (CMV), Epstein-Barr Virus (EBV), varicella zoster virus (VZV), HHV-6, and HHV-7.

Maturation of herpes virus particles is believed to occur through the formation of a procapsid structure, which acquires DNA and an envelope to become an infectious virion. A herpes virus group-common protein referred to as the assembly protein in CMV, and as p40, VP22a, NCP-3, and ICP35e in HSV-1, is an abundant constituent of the herpes virus procapsid. The assembly protein is phosphorylated and proteolytically processed from a precursor molecule. It is absent from the mature virion, although its fate is unknown. These characteristics of the assembly protein have suggested an analogy between it and the bacteriophage scaffolding protein, which is an essential component for phage assembly but is not found in mature virus particles (Gibson et al. (1991) J. Virol. 64:1241–1249).

The proteolytic processing of the assembly protein has been implicated as a critical step in the maturation of the virus. A temperature sensitive (ts) mutant that is unable to process the HSV assembly protein homolog (p40) is incapable of producing DNA-containing capsids or virions (Preston et al. (1983) J. Virol. 45:1056–1064). Maturational processing of the simian CMV (SCMV) Colburn assembly protein results in loss of its carboxy terminus. (Gibson, 1991, supra.)

Up until the present time the enzyme responsible for the proteolytic maturation of the assembly protein has not been identified. Further, there is a need in the art for new agents for therapeutic treatment of herpes viruses.

SUMMARY OF THE INVENTION

It is an object of the invention to provide a preparation of a proteinase encoded by a herpes virus.

It is another object of the invention to provide a substrate for cleavage by a herpes virus proteinase.

It is yet another object of the invention to provide a kit for measuring activity of a herpes virus proteinase.

It is still another object of the invention to provide a method for measuring activity of a herpes virus proteinase.

It is another object of the invention to provide a recombinant DNA molecule which encodes a herpes virus proteinase.

It is yet another object of the invention to provide an inhibitor of a herpes virus proteinase.

These and other objects of the invention are provided by one or more of the embodiments described below.

In one embodiment of the invention a preparation of the proteinase encoded by a herpes virus is provided, said preparation being free of a intact infectious herpes virus virion DNA.

In another embodiment of the invention substrates for cleavage by a herpes virus proteinase are provided. One substrate comprises a polypeptide containing the amino acid sequence:

$aa_1$-$aa_2$-Ala-$aa_3$ (SEQ ID NO:28–30), wherein $aa_1$ is Val or Leu, $aa_2$ is a polar amino acid, and $aa_3$ is Ser, Val, or Asn, wherein the proteinase cleaves the substrate on the carboxy terminal side of the Ala residue. Another substrate comprises a polypeptide containing the amino acid sequence:

Tyr-$aa_4$-$aa_5$-Ala-$aa_6$ (SEQ ID NO:32), wherein $aa_4$ is Val or Leu, $aa_5$ is Lys or Gln and $aa_6$ is Ser or Asn, and wherein the proteinase cleaves the substrate on the carboxy terminal side of the Ala residue.

In yet another embodiment of the invention a kit is provided for measuring activity of a herpes virus proteinase. The kit comprises a proteinase encoded by a herpes virus, and a substrate for cleavage by said proteinase. The substrate comprises a polypeptide containing the amino acid sequence:

$aa_1$-$aa_2$-Ala-$aa_3$ or

Tyr-$aa_4$-$aa_5$-Ala-$aa_6$ (SEQ ID NO:28, 29, 30 or 32), wherein $aa_1$ is Val or Leu, $aa_2$ is a polar amino acid, $aa_3$ is Ser, Val, or Asn, $aa_4$ is Val or Leu, $aa_5$ is Lys or Gln and $aa_6$ is Ser or Asn, wherein the proteinase cleaves the substrate on the carboxy terminal side of the Ala residue, said kit being substantially free of intact infectious herpes virus.

In still another embodiment of the invention a method is provided for measuring activity of a herpes virus proteinase. The method comprises the steps of: contacting a proteinase encoded by a herpes virus with a substrate for cleavage by said proteinase, said substrate comprising a polypeptide containing the amino acid sequence;

$aa_1$-$aa_2$-Ala-$aa_3$ or

Tyr-$aa_4$-$aa_5$-Ala-$aa_6$ (SEQ ID NO:28, 29, 30or 32)

wherein $aa_1$ is Val or Leu, $aa_2$ is a polar amino acid, $aa_3$ is Ser, Val, or Asn, $aa_4$ is Val or Leu, $aa_5$ is Lys or Gln and $aa_6$ is Ser or Asn, wherein the proteinase cleaves the substrate on the carboxy terminal side of the Ala residue, said step of contacting occurring in the absence of an intact infectious herpes virus virion DNA; and monitoring cleavage of said substrate.

In another embodiment of the invention a recombinant DNA molecule is provided which encodes at least a portion of the herpes virus proteinase, said portion having the ability to cleave a herpes virus assembly protein precursor.

In yet another embodiment of the invention an inhibitor of a herpes virus proteinase is provided. The inhibitor comprises a derivative of the substrate of the herpes virus proteinase. The inhibitor may differ from the substrate in the scissile peptide bond which is carboxyl to the Ala residue.

These, and other embodiments of the invention which will be obvious to one skilled in the art from the disclosure, are described in more detail below. These embodiments provide the art with a promising target for specific anti-viral therapeutic agents, which can be administered to humans and other animals without also impairing normal cellular functions.

BRIEF DESCRIPTION OF THE DRAWINGS

FIGS. 1A, 1B, 1C, and 1D show the nucleotide (SEQ ID NO:1) and predicted amino acid (SEQ ID NO:2) sequences of the CMV Colburn genomic region containing the assembly protein gene at the 3' end of a 1,770-base pair open reading frame. The open reading frame, designated APNG1, denotes the beginning of the coding sequence of the proteinase gene, and the open reading frame designating APNG.5 denotes the beginning of the coding sequence of the precursor assembly protein gene. Each of the four designated open reading frames are in frame and are 3' co-terminal.

FIG. 2 shows a comparison of portions of the putative active site domains of the proteinase in (HCMV) Colburn (SEQ ID NOS:16and 17), located between amino acids 15 and 195 and those in other herpes viruses. Two highly conserved motifs within this region are also identified in human CMV (SEQ ID NOS:18 and 19), herpes simplex virus-1 (HSV-2), varicella zoster (VZV) virus, Epstein-Barr (EBV) virus, and infectious laryngotracheitis virus (ILTV) (SEQ ID NOS:26 and 27). The absolutely conserved amino acids are shown in bold type.

FIGS. 3A and 3B show the cleavage site in the assembly protein of SCMV (SEQ ID NO:3), located between amino acids $Ala_{557}$ and $Ser_{558}$. This region is shown as compared to homologous and conserved regions in other herpes viruses. Absolutely conserved amino acids are shown in bold type. The arrow in the sequence denotes the cleavage site. FIG. 3B shows the cleavage site for release of the herpesvirus proteinase from the primary translation product of the APNG1 gene is located in six herpes viruses between amino acids 234 and 262 (SEQ ID NOS:4–9). Absolutely conserved amino acids are shown in bold type. The space following the alanine residue denotes the cleavage site.

DETAILED DESCRIPTION

Figure 4:
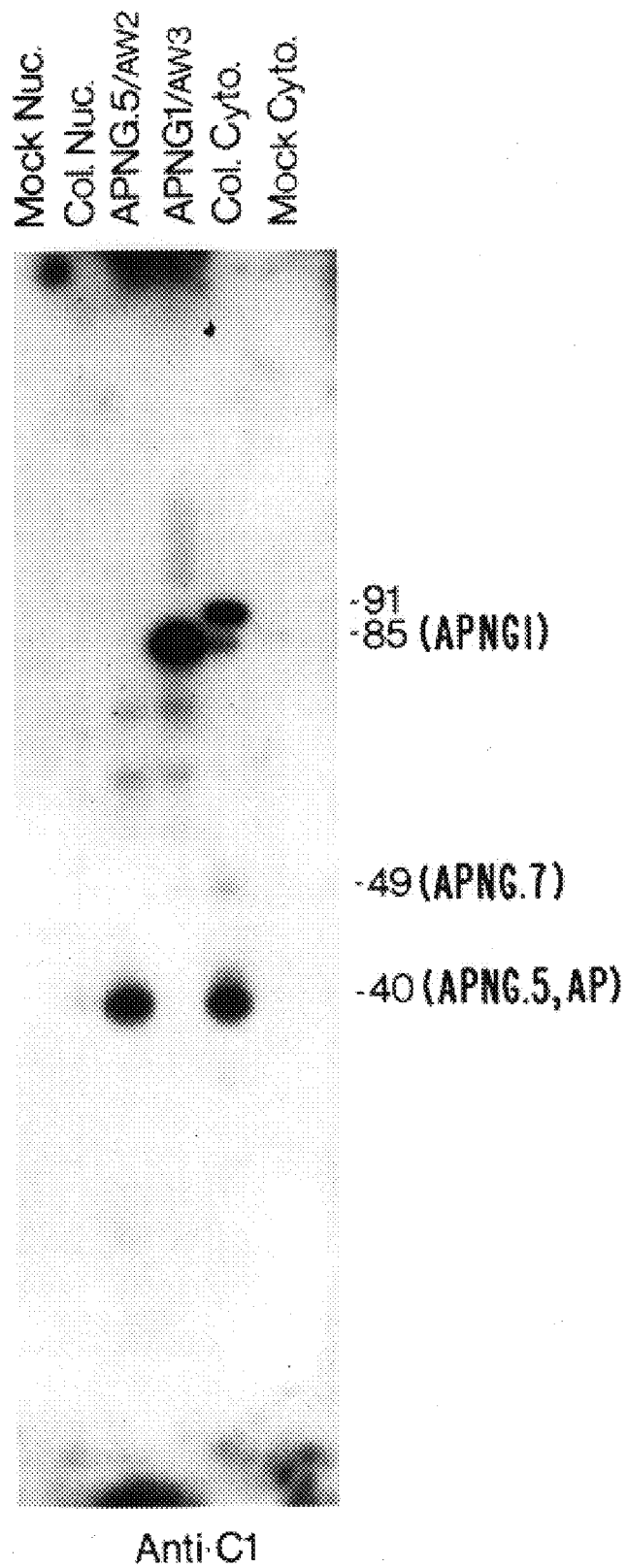
FIG. 4 shows products of an in vitro transcription and translation of the cloned CMV Colburn assembly protein gene (APNG.5) as well as the cloned proteinase gene (APNG1). Proteins are revealed by their reactivity with antibodies (i.e., Anti-C-1) reactive only with noncleaved assembly protein nested gene products.

It is a finding of the present invention that the assembly protein of herpes viruses is maturationally processed by a herpes virus-encoded proteinase. Fascinatingly, the proteinase has been found to be a member of a family of four nested 3' co-terminal genes which includes the assembly protein itself. Each of the genes appears to be transcribed into separate mRNAs.

It appears that proteolytic cleavages may occur in this family of gene products at a number of locations. One such location, which has been identified with certainty, is the cleavage site within the assembly protein precursor itself. This site occurs between the alanine at amino acid position 557 and the serine at amino acid position 558 in the CMV Colburn APNG1 gene product (SEQ ID NO:2). [Amino acid numbering in this application begins with the first putative initiation codon of APNG1 shown in FIG. 1 as the first underlined methionine codon.] The cleavage site in herpes virus assembly protein precursors have the conserved motif of $aa_1$-$aa_2$-Ala-$aa_3$ (SEQ ID NOS:28–30), wherein $aa_1$ is Val or Leu, $aa_2$ is a polar amino acid, and $aa_3$ is Ser, Val, or Asn. This cleavage site is herein referred to as the assembly protein maturation cleavage site. Another putative cleavage site within this family of nested proteins occurs after the Ala residue of the sequence Tyr-Val-Lys-Ala, which occurs at amino acids 246 to 249 in the CMV Colburn APNG1 gene product. This site has been used as the carboxy terminus of a recombinant construct, and the construct has been found to have proteinase activity. This suggests that this site may be used in vivo for autoprocessing of the proteinase molecule. The cleavage site in the primary translation product of the gene encoding for herpes virus proteinase have the conserved motif of Tyr-$aa_4$-$aa_5$-Ala-$aa_6$ (SEQ ID NO:32), wherein $aa_4$ is Val or Leu, $aa_5$ is Lys or Gln and $aa_6$ is Ser or Asn. This cleavage site is herein referred to as the enzyme release cleavage site. Both the maturation cleavage site and the enzyme release cleavage site in SCMV are highly conserved among herpes viruses as shown in FIGS. 3A and 3B.

SEQ ID NOS 3–9 show the maturational and cleavage site, located between numbered amino acids 11 and 12 in the assembly protein of CMV Colborne, HCMV, HSV-1, VZV, EBV, ILTV and HSV-6, respectively.

SEQ ID NOS 10–15 show the enzyme cleavage site located between numbered amino acid 10 and 11, for the release of the herpesvirus proteinase of CMV Colborne, HCMV, HSV-1, VZV, EBV and ILTV, respectively.

According to the present invention a preparation of proteinase encoded by a herpes virus is provided. The preparation is substantially free of intact infectious herpes virus virion DNA. Virion DNA refers to the DNA which is present in viral particles. Preparations of the present invention can be provided which are totally free of virion DNA because they are produced in cells which have been transfected with a recombinant construct encoding the proteinase. Thus cells producing the proteinase may not ever have been infected with herpes virus. The herpes virus proteinase from cytomegalovirus (CMV, simian strain Colburn) is encoded by a 1,770 base pair gene referred to APNG1(assembly protein nested gene 1). The nucleotide and amino acid sequence of this gene is shown in SEQ ID NO 1. SEQ ID NO 2 shows only the amino acid sequence shown in SEQ ID NO 1. This gene has homologs in human CMV (HCMV, i.e., UL80a), herpes simplex virus-1 (HSV-1, i.e., UL26), varicella zoster virus (VZV, i.e., UL33), Epstein-Barr virus (EBV, i.e., BVRF2), infectious laryngotracheitis virus (ILTV, i.e., p40 gene), and probably in all herpes viruses. A proteinase according to the present invention may be all or an active portion of the APNG1primary translation product, or its homologs on other herpes viruses. As previously alluded to, not all of the APNG1 primary translation product is necessary for proteinase activity. For example, constructs which have only the first 249 (LM8) or first 280 (LM7) amino acids beginning with the initial methionine codon on the APNG1 gene both demonstrate proteinase activity. Activity is defined as the ability to proteolytically process the assembly protein precursor of herpes virus to the mature assembly protein or to cleave site mimetic substances.

The preparation of proteinase of the present invention may be made in cells by recombinant DNA techniques, but need not be. The protein may be expressed in mammalian cells, as well as in bacterial, yeast, insect cells, and other cell types, as is convenient for a particular application or purpose. Alternatively, the protein can be chemically synthesized, or expressed in vitro using an in vitro transcription and/or translation system. In still another method of obtaining such a proteinase preparation, infected cells can be used as a source material and standard protein purification techniques can be used. Such purification techniques will typically include an affinity separation step (e.g., immunoaffinity; substrate affinity).

The active site domain of the proteinase enzyme has been tentatively identified as the region between and including amino acids 15 (Asp) and 95 (Ser) in the CMV Colburn APNG1 proteinase (SEQ ID NO:2). This region contains two motifs that are highly conserved among the homologous genes of HCMV, HSV-1, VZV, EBV, ILTV, and probably all herpes viruses. See FIG. 2 and SEQ ID NOS:16–27. These motifs are referred to as conserved motif 1 and conserved motif 2.

SEQ ID NOS 17–27 correspond to conserved motif 1 of CMV Colburne, HCMV, HSV-1, VZV, EBV and ILTV, respectively.

SEQ ID NOS 16–26 correspond to conserved motif 2 of CMV Colburne, HCMV, HSV-1, VZV, EBV and ILTV, respectively. A recombinant construct of the proteinase gene was made having a 15 amino acid insertion between conserved motifs 1 and 2. This construct had greatly diminished (i.e., less than about 1% of the wild-type level) proteinase activity, which supports the assignment of the active site domain.

The cleavage site in the assembly protein precursor (i.e., the maturation cleavage site) which leads to formation of the mature assembly protein has been defined with particularity. In simian CMV (Colburn) the cleavage site has been defined as occurring between amino acids 557 and 558 (SEQ ID NO:2). The sequence immediately surrounding this site is Val-Asn-Ala-Ser-Cys. When the assembly protein sequences of other herpes viruses are compared it is found that this site is well conserved. (See FIG. 3 and SEQ ID NOS:3–9). The consensus cleavage site appears to require $aa_1$-$aa_2$-Ala-$aa_3$, wherein $aa_1$ is Val or Leu, $aa_2$ is a polar amino acid, and $aa_3$ is Ser or Val. The amino acid represented as $aa_2$ is most often an asparagine residue.

While not wishing to be bound by any particular theory, there is evidence (Welch et al. (1991) Proc. Natl. Acad. Sci. U.S.A., in press) that an additional cleavage site or sites for the proteinase occurs near the middle of the proteinase sequence. It is likely that the proteinase which is responsible for the maturational cleavage of the assembly protein is also involved in self-processing, possibly to create an active form of the proteinase. The carboxyl half of the APNG1 gene product has been identified in transfected cells, indicating that cleavage in the middle of the APNG1 primary translation product is biologically relevant. (See FIG. 5, APNG1$_c$.) Cleavage at this site (i.e., the enzyme release cleavage site) may be required for the life cycle of the herpes viruses. The consensus sequence for this site comprises Tyr-$aa_4$-$aa_5$-Ala-$aa_6$ (SEQ ID NO:32), wherein $aa_4$ is Leu or Val, $aa_5$ is Lys or Gln, and $aa_6$ is Ser or Asn.

Having defined the actual cleavage site in the assembly protein precursor and putative cleavage site in the proteinase, it is now possible to design smaller synthetic moieties which can be used as substrates for cleavage by the herpes virus proteinase. These substrates for cleavage typically comprise a polypeptide having an amino acid sequence which has been shown to be a recognized cleavage site by a herpes virus proteinase. The polypeptides will contain the amino acid sequence $aa_1$-$aa_2$-Ala-$aa_3$ (SEQ ID NOS:28–30) or Tyr-$aa_4$-$aa_5$-Ala-$aa_6$ (SEQ ID NO:32), and most often will contain the amino acid sequence $aa_1$-$aa_2$-Ala-Ser or Tyr-$aa_4$-$aa_5$-Ala-Ser. The substrate is substantially free of the assembly protein precursor or the entire primary translation product of the gene encoding the herpes virus proteinase. This is possible because the entire assembly protein precursor or the entire primary translation product of the gene encoding the proteinase need not be used as a substrate. Synthetic or recombinant substrates can be made which are recognized and cleaved by a herpes virus proteinase. Substrates for the proteinase will typically comprise a polypeptide portion of between about 15 and 25 amino acids. A sufficient number is required for the proteinase to be able to recognize and bind to the cleavable site. Extraneous amino acids are not desirable because they may cause steric inhibition by formation of three-dimensional structures which block the cleavage site. Substrates which mimic the maturation cleavage site or the enzyme release cleavage site can also be made.

The substrate itself need not be a totally proteinaceous molecule. It may be linked to other moieties and polymers as is convenient. The substrate will typically be used for assaying proteinase activity in cellular extracts or in synthetic proteinase preparations, as described above, as well as for screening for inhibitory substances which block the proteinase cleavage reaction. In one embodiment of the present invention the polypeptide portion of the substrate is linked to a fluorescent moiety and a quenching moiety. Typically these will be linked on opposite ends of the polypeptide. While linked to the polypeptide the fluorescent moiety will not fluoresce due to the proximity of the quenching moiety. However, upon cleavage of the polypeptide, the separation of the two moieties will lead to a loss of quenching and to detectable fluorescence. An example of a similar quenched fluorogenic substrate is taught by Matayoshi, et al. (Science (1990) 247:954–958). There the fluorogenic and quenching moieties employed are 4-(4-dimethylaminophenylazo)benzoic acid (DABCYL) and 5-[(2-aminoethyl)amino]naphthalane-1 sulfonic acid (EDANS). As another example of an indicator substrate, a substrate having the cleavage site engineered into a protein, such as β-galactosidase or luciferase, so that cleavage inactivates the activity of the indicator, is mentioned.

In another embodiment of the invention the substrate for cleavage of a herpes virus proteinase is labeled with a radioactive moiety. After exposure of the substrate to the proteinase, the chemical or physical properties of the radioactive species can be determined, specific changes in these properties can be used to monitor cleavage by the proteinase. One such property is size, a reduction in size of the radioactive species indicating cleavage by the proteinase. Alternatively, after exposure of the substrate to the proteinase, the substrate can be extracted into a solvent. A change in the extractability of the radioactive species can be used to indicate cleavage of the substrate. In yet another embodiment of the invention an enzyme is linked to the polypeptide comprising the cleavage site. The polypeptide sterically inhibits the activity of the enzyme. However, upon cleavage of the polypeptide moiety the steric inhibition is relieved and the enzyme activity is regained and can be assayed. Increase of enzyme activity therefore is an indication of cleavage. In an alternative embodiment, the substrate for the enzyme which is linked to the polypeptide for cleavage is also linked to the polypeptide for cleavage. Again, the enzyme is sterically inhibited by its linkage to the polypeptide. However, upon cleavage of the polypeptide the steric inhibition is released and the enzyme can interact with its substrate.

Having discovered the proteinase of herpes virus and its particular sites for cleavage (i.e., the maturation cleavage site and the enzyme release cleavage site), a kit can be readily prepared for measuring the activity of a herpes virus proteinase. The kit comprises a proteinase, or portion thereof, encoded by herpes virus and a substrate for cleavage by said proteinase. The substrate for cleavage has the properties described above. Briefly, a substrate for cleavage contains a polypeptide having the amino acid sequence $aa_1$-$aa_2$-Ala or Tyr-$aa_4$-$aa_5$-Ala, and the proteinase cleaves the substrate on the carboxy terminal side of such sequences. The kit is substantially free of intact infectious herpes virus. This purity can be achieved in a number of ways. Preferably, it can be achieved by expressing the proteinase and the substrate for cleavage in a mammalian cell which is free of herpes virus infection. The cleavage of the substrate occurs within the mammalian cell and can be monitored by observation of a change in the size of the substrate, for example. Alternatively, the proteinase and the substrate can be expressed in an in vitro cell-free system, such as a rabbit reticulocyte system, or synthesized chemically. In such cases the two components of the kit can be contacted in vitro and the cleavage reaction observed. The proteinase and the substrate can also be expressed in separate cells of any suitable species. The cells may be either mammalian, bacterial, yeast, insect, or other cell type, as is convenient for the particular application involved. After separately expressing the proteinase and its substrate they can be contacted in vitro to determine an amount of herpes virus proteinase activity.

In another embodiment of the invention, the cleavage reaction can be used diagnostically to test for the presence of a herpes virus. For example, putatively infected cells can be used as a source of proteinase and contacted with a substrate for cleavage. The cleavage of the substrate would indicate the presence in the source of a herpes virus proteinase and therefore of a herpes virus infection.

Also contemplated by the present invention is a method for measuring activity of a herpes virus proteinase. According to the method, a proteinase encoded by a herpes virus is contacted with a substrate for cleavage by the proteinase. The substrate for cleavage has the properties described above. The contacting of the substrate with the proteinase occurs in the absence of intact infectious herpes virus virion DNA; this can be accomplished by using as sources of substrate and proteinase cells which are not infected with a herpes virus. The second step of the method involves monitoring cleavage of the substrate. Such monitoring can be accomplished by determining a change of size of said substrate, for example, by observing an altered mobility of the substrate on an electrophoretic gel matrix or on a chromatography medium. Alternatively, the monitoring can be accomplished by observing a change of fluorescence if the substrate has been labelled with a fluorescent moiety as described above. If the substrate has been labelled with a radiolabelled moiety then the cleavage reaction can be monitored by looking for a change in its physical properties, as described above. In another embodiment a substrate that has been labelled with an enzyme is used and the cleavage reaction is monitored by determining a colorimetric change of a chromogenic substrate for the enzyme. Suitable enzymes for such purposes are known in the art and include β-galactosidase, alkaline phosphatase, and luciferase.

In one embodiment of the method of the present invention, a test substance is also added to the proteinase (or active portion thereof) and substrate to determine the level of inhibition caused by the test substrate. This method can be used as a screen for potential therapeutic molecules. The level of inhibition can be readily determined by measuring the activity of the proteinase in the presence and absence of the test substrate. A significant diminution of the activity of the proteinase in the presence of the test substance indicates a potential anti-herpetic agent.

Inhibitors of the herpes virus proteinase are also provided by the present invention. Typically, these are non-cleavable derivatives of substrates of the proteinase. The inhibitors may comprise a polypeptide portion of about 6 to 12 amino acids and often will mimic the structure of the appropriate substrate for the proteinase. However, the inhibitor may differ from the substrates for the enzyme in having a modification of the scissile peptide bond which is carboxyl to the sequence $aa_1$-$aa_2$-Ala (SEQ ID NOS:28–30) or Tyr-$aa_4$-$aa_5$-Ala (SEQ ID NO:32). Any modification of this bond can be used which partially inhibits or totally blocks the proteinase cleavage. Such modifications of the scissile peptide bond include replacement by a hydroxyethylamine linkage, a phosphonamide linkage, a carbon fluoride aldehyde, and a dialcohol linkage. Such inhibitors will bind to the proteinase active site domain but will be either totally non-cleavable or cleavable at a much lower rate than a proper substrate. As the cleavage reaction is known to be essential for the formation of herpes virus particles, inhibition of the cleavage reaction can be used as an anti-herpetic therapeutic treatment.

Certain modifications to the inhibitors of the present invention may be desired in order to render them more resistant to proteolysis in the human body or to render them more easily taken up by infected cells. One such modification is to place an amide moiety on the carboxy terminal end of the polypeptide. This reduces the charge of the molecule rendering it more accessible to cells. Another possible modification involves placing a D-tyrosine moiety on the amino terminal end of the inhibitor. This renders the inhibitor less susceptible to proteolysis.

Other inhibitors may now be designed based on the 3-dimensional structure of the proteinase. Typically, X-ray crystallography is used to determine a structure for the enzyme and inhibitors are designed to conform to the determined structure. Since it has been shown that proteinase activity resides within the first 249 amino acids of the CMV Colbourn APNG1 protein, the use of X-ray crystallography to determine the 3-dimensional structure of the amino terminal 249 residues can be used to design inhibitors of this proteolytically active sequence.

Recombinant DNA molecules are also provided by the present invention. These molecules encode at least a portion of the herpes virus proteinase. The proteinase portion retains the ability to cleave a herpes virus assembly protein. Applicants have found that the entire proteinase gene which is transcribed in vivo as a 1.8 kb RNA molecule, is not necessary for expression of proteinase activity. It has been determined that the portion of the APNG1 gene encoding the assembly protein precursor is not needed for proteolytic activity. Portions of the proteinase which comprise only amino acids 1 through 249 have been found to retain proteolytic activity. Further, as discussed above, it is possible that further shortening of the proteinase molecule is possible without loss of proteolytic activity.

EXAMPLES

Example 1

This example provides the sequence of the simian CMV proteinase gene and compares portions of it to other herpes virus sequences.

The XbaI R fragment of strain Colburn CMV DNA was cloned into the plasmid pUC18, and the nucleotide sequence of both strands was determined by the dideoxy nucleotide chain termination method (Sanger et al., Proc. Natl. Acad. Sci. U.S.A. (1977) 74:5463–5467) with appropriate DNA oligonuycleotide primers and the Sequenase kit (USB, Cleveland, Ohio).

Nucleotide sequence analysis of the CMV (Colburn) genomic XbaI R fragment confirmed the cDNA sequence previously determined for the assembly protein-coding region and revealed that the 930-bp coding sequence for the assembly protein precursor (nucleotides 1072 to 2001) is the 3' end of a 1,770-bp open reading frame (ORF) (nucleotides 232 to 2001) that begins with a methionine and, together with its upstream regulatory region, was designated assembly protein nested gene 1 (APNG1) (FIG. 1). APNG1 includes an upstream potential TATA promoter element, contains three internal potential TATA promoters and three corresponding ATG translational start codons in addition to its own, and is followed by a single downstream polyadenylation signal. This organization indicated that the APNG1 region could give rise to four 3'-coterminal mRNAs able to encode four corresponding in-frame, overlapping proteins. These nested coding sequences are numbered according to their fractional length relative to that of the longest, APNG1. FIG. 1 presents the nucleotide and amino acid sequences of the APNG1 region and shows the positions of (1) proposed TATA promoter elements (italicized and dot underlined), (2) proposed translational start methionines for the coding sequence in each of the nested genes (capitalized and doubly underlined, and the designation of the corresponding assembly protein nested gene (APNG) is indicated above each), (3) the single polyadenylation signal at the 3' end (underlined). The APNG1 (proteinase) gene has homologs in human CMV (HCMV, i.e., UL80a), herpes simplex virus type-1 (HSV-1, i.e., UL27), varicella zoster virus (VZV, i.e., UL33), Epstein-Barr virus (EBV, i.e., BVRF2), and infections laryngotracheitis virus (ILTV, i.e., p40).

At least a portion of the active site domain of the proteinase has now been tentatively identified as the region between amino acids 15 and 195 in the CMV Colburn APNG1 protein. This region contains two motifs that are highly conserved among the homologous genes of HCMV, HSV-1, VZV, EBV, and ILTV, and probably all herpes viruses (FIG. 2). These motifs are referred to as "conserved motif 1" (CM1) and "conserved motif 2". Striking similarities in the spacing of possible active site residues resembling both cysteine (i.e., $His_{47}$, $Cys_{146}$, $His_{-142}$) and serine ($His_{47}$, $Asp_{104}$, $Ser_{195}$) proteinases are detected among all six herpes viruses, suggesting that the herpes virus proteinases may have two separate proteolytic activities.

Figure 5:
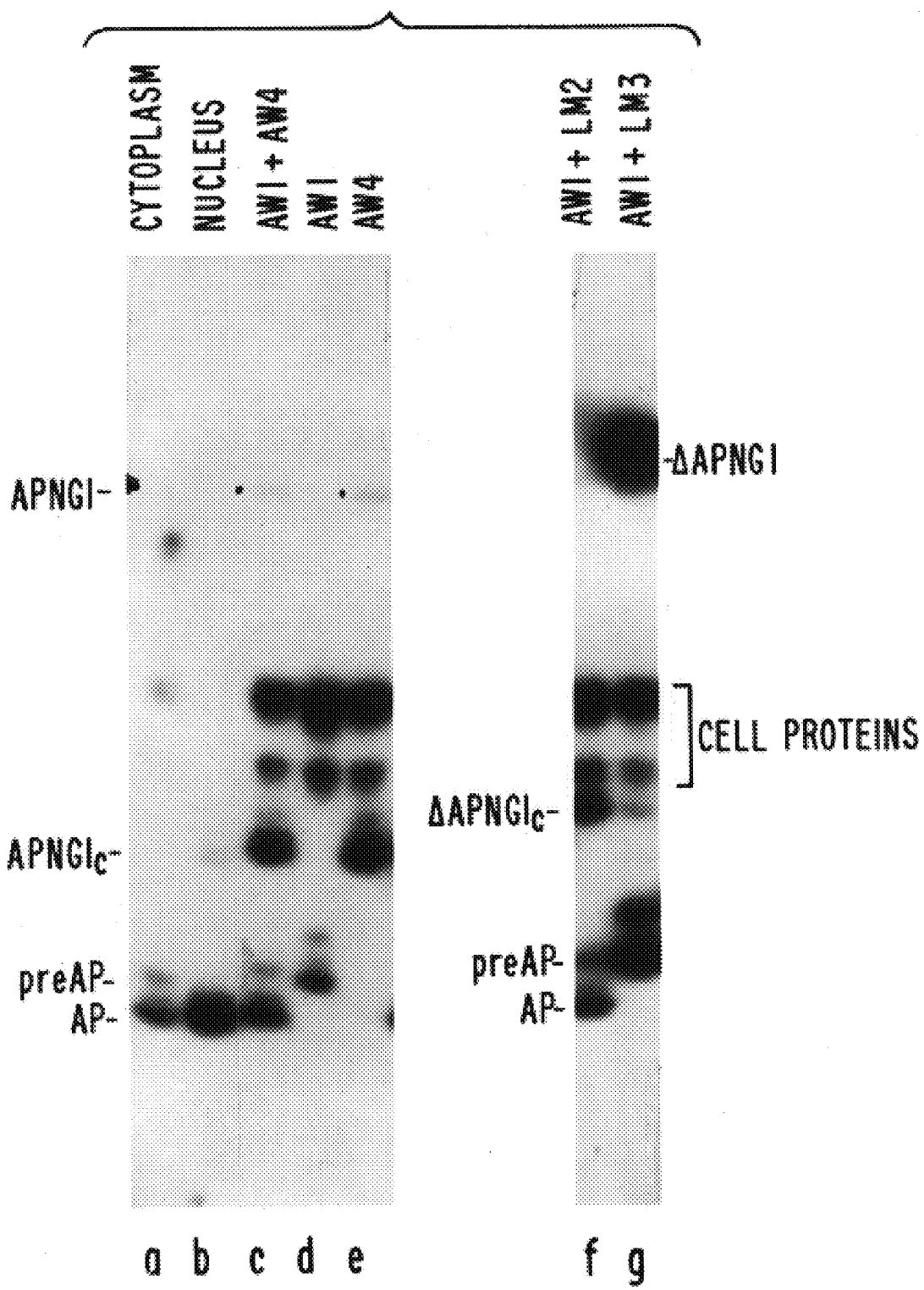
FIG. 5 shows that assembly protein cleavage occurs in cells cotransfected with the genes for the assembly protein precursor (APNG.5/AW1) and for the proteinase (APNG1/AW4).

It has been found that an altered form of APNG1 (LM3) which contains a 15 amino acid sequence (the C3 epitope of poliovirus VP2) inserted between CM1 and CM2, has only a trace amount of proteinase activity (i.e., $\leq 1\%$) (see FIG. 5, lane g). Insertion of the same sequence into the carboxyl end of APNG1 did not reduce proteinase activity (FIG. 5, lane f). This suggests that the CM1/CM2 region does contain at least a portion of the active site domain of this proteinase.

Furthermore, two subclones of APNG 1 were made which expressed portions of the proteinase gene comprising amino acids 1–249 (LM8) and 1–280 (LM7). Both are proteolytically active using assembly protein precursor as a substrate. This, too, supports the active site domain assignment.

Example 2

This example demonstrates the precise cleavage site involved in the maturational processing of assembly protein precursor to assembly protein, as well as the conservation of the site among herpes viruses.

The mature assembly protein was treated with endoproteinase Lys-C or endoproteinase Glu-C (V8 proteinase). Specific peptide products were isolated and subjected to analysis by mass spectrometry. The diagnostic molecular ions identified from HPLC-purified peptides of the Colburn CMV assembly protein were mass 902.5 (Endo-Lys-C fragment, SAERGVVNA) and mass 616.4 (Endo-Glu-C fragment, RGVVNA) (SEQ ID NO:2). Thus the cleavage site is between $Ala_{557}$ and $Ser_{558}$ in SCMV Colburn. This cleavage site is well conserved in HCMV, HSV-1, VZV, EBV, ILTV, and probably in all herpes group viruses (FIG. 3).

Example 3

This example provides proteinase substrate derivatives with altered chemistry at the scissile peptide bond.

Based on the cleavage site sequence, several classes of anti-herpes virus peptide mimetics can be synthesized. These include hydroxyethylamine-, dialcohol-, phosphonamide-, and carbon fluoride aldehyde-derivatives of the scissile peptide bond (i.e., carboxyl to the alanine in the general sequences $aa_1$-$aa_2$-Ala-$aa_3$ (SEQ ID NOS:28–30) and Tyr-$aa_4$-$aa_5$-Ala-$aa_6$ (SEQ ID NO:32) such as:

$aa_1$-$aa_2$-Ala-CHOH—$CH_2$—NH-$aa_3$ (hydroxyethylamine derivative)

$aa_1$-$aa_2$-Ala-$PO_2$—NH-$aa_3$ (phosphonamide derivative)

$aa_1$-$aa_2$-Ala-$CF_2$CHO (carbon fluoride aldehyde)

$aa_1$-$aa_2$-Ala-$C(OH)_2$—NH-$aa_3$ (dialcohol derivative)

Tyr-$aa_4$-$aa_5$-Ala-CHOH—$CH_2$—NH-$aa_6$ (hydroxyethylamine derivative)

Tyr-$aa_4$-$aa_5$-Ala-$PO_2$—NH-$aa_6$ (phosphonamide derivative)

Tyr-$aa_4$-$aa_{Ala-CF2}$—CHO (carbon fluoride aldehyde)

Tyr-$aa_4$-$aa_5$-Ala-$C(OH_2)$—NH-$aa_6$ (dialcohol derivative)

Example 4

This example demonstrates the in vitro transcription and translation of the cloned CMV Colburn assembly protein precursor gene.

The assembly protein precursor gene (APNG.5, see FIG. 1) and the overlapping APNG1gene were cloned from the simian strain Colburn CMV DNA, using PCR amplification, into a pGEM4Z plasmid to produce plasmids AW2 and AW3, respectively. T7-promoted run-off transcripts of both genes were prepared, and translated in rabbit reticulocyte lysates containing $^{35}$S-methionine. The proteins were separated by electrophoresis in an SDS-containing polyacrylamide gel (10%), electrotransferred onto an Immobilon-P™ membrane and probed with an antiserum to the carboxyl 21 amino acids of the assembly protein precursor (i.e., Anti-C1, see Schenk, et al. (1991) J. Viol. 65: 1525–1529). The resulting protein-antibody complexes were visualized by using $^{125}$I-Protein A. A fluorogram of the blot is shown in FIG. 4. The exposure technique used recorded only $^{125}$I-radioactivity (i.e., Kodak DEF film and black paper between blot and recording Kodak XAR film).

The in vitro translated assembly protein (lane 3, APNG.5/AW2) comigrated with the infected cell assembly protein precursor (i.e., 40-kDa band in lane 5) and was not proteolytically processed in the reticulocyte lysate. The protein product of the APNG1 gene (lane 4) comigrated with the 85-kDa protein present in the Colburn CMV-infected cell cytoplasm (i.e., 85-kDa band in lane 5). Mock infected nuclear and cytoplasmic fractions (lanes 1 and 6) show no evidence of proteins reactive with the Anti-C1 antibody.

Example 5

This example demonstrates that assembly protein cleavage occurs in cells cotransfected with the genes for the assembly protein precursor and for the APNG1 protein.

Human cells were transfected with an expression plasmid containing the gene for the assembly protein precursor (AW1), or with an expression plasmid containing the gene for the APNG1protein (AW4), or with both plasmids (AW1+AW4). Parallel cotransfections were done using the AW1 plasmid in combination with altered versions of AW4 that contain (1) a 13 amino acid sequence inserted into the carboxyl end of APNG1 (LM2), or (2) a 15 amino acid sequence inserted into the amino end of APNG1 (LM3).

Following transfection the cells were solubilized and the proteins were separated by electrophoresis in an SDS-containing polyacrylamide gel (SDS-PAGE). The resolved proteins were electrotransferred to an Immobilon-P™ membrane and visualized by probing the membrane with an antiserum (Anti-N1) that reacts with the amino end of the assembly protein and with other assembly protein nested gene products (e.g., 85-kDa APNG1 protein). Colburn CMV-infected cell proteins were run as markers. The results of these experiments are shown in FIG. 5.

The assembly protein (AP) and its precursor (preAP) can be seen in the cytoplasmic and nuclear fractions of Colburn CMV-infected cells (lanes a and b, respectively). The precursor form is more abundant in the cytoplasm (lane a) and the mature form is more abundant in the nucleus (lane b).

Cells transfected with only the gene coding for the assembly protein precursor (i.e., plasmid AW1) expressed the precursor form of the assembly protein but no product (lane d). The much less abundant, slightly larger protein is believed to correspond to a protein also detected in infected cells, but present there in vanishingly small amounts.

Cells transfected with only the gene coding for the larger protein of the "assembly protein nested gene family" (i.e., 85-kDa protein product of APNG1 encoded by plasmid AW4) expressed the 85k-Da protein (APNG1), and a second doublet band believed to represent the carboxyl end of the APNG1 protein (i.e., APNG1$_c$, 45- to 50 kDa in size, lane e).

Cells cotransfected with the assembly protein precursor gene and the APNG1 gene (i.e., AW1+AW4) contained: (1) the APNG1 and APNG1$_c$ proteins encoded by AW4, and (2) predominantly the mature (i.e., cleaved) form of the assembly protein (AP) (lane c). Essentially no precursor form of the assembly protein (preAP) was detected with this serum (Anti-N1) or with an even more sensitive antiserum for the precursor form (i.e., Anti-C1). This finding indicates that cleavage of the precursor in transfected cells is highly efficient.

Cells cotransfected with the assembly protein precursor gene (AW1) and an altered form of the APNG1 gene (LM2, altered at the carboxyl end) that contains a 45 bp insert at the single APNG1 DraI site, encoding the polio virus VP2 C3 epitope (Charbit, et al., 1986, EMBO J., vol. 5, pp. 5029–3038) contained: (1) a higher molecular weight form of APNG1 (ΔAPNG1, indicated by dot to left of lane f) resulting from the inserted 15 amino acids of VP2 C3, (2) a correspondingly larger form of the carboxyl end of the APNG1 protein (i.e., ΔAPNG1$_c$), and (3) only the mature (i.e., cleaved) form of the assembly protein (AP)(lane f). The band close to the position of the assemblyprotein precursor (i.e., preAP) in lane 4 is not reactive with Anti-C1 and is believed to correspond to the processed form of the slightly larger, low abundance protein expressed by AW1 and mentioned above.

Cells cotransfected with the assembly protein precursor gene (AW1) and an altered form of the APNG1 gene (LM3, altered at amino, N'-end) that contains a 45 bp insert (VP2 C3) at the single APNG1 EcoRV site, located between the highly conserved motifs CM1 and CM2, contained: (1) a higher molecular weight form of APNG1 (ΔAPNG1, indicated by arrow to left of lane g) resulting from the inserted 15 amino acids of VP2 C3, (2) a weak band at the position of ΔAPNG1$_c$, but corresponding in size to the band in lane f because the carboxyl cleavage at Val-Asn-Ser has not occurred (i.e., band in lane g reacted with Anti-C1, in contrast to band in lane f), and (3) only the noncleaved, precursor form of the assembly protein (preAP)(lane g). Again, the lower abundance band above the assembly protein precursor in lane g is thought to correspond to a scarce species also detected in infected cells.

We claim:

1. A proteinase substrate for cleavage by a herpes virus proteinase, said substrate comprising a polypeptide consisting of not more than about 25 L-isomer amino acids, said polypeptide containing an amino acid sequence:

$aa_1$-$aa_2$-Ala-$aa_3$, wherein (a) $aa_1$ is Leu, $aa_2$ is Gly, Ser, Thr, Cys, Tyr, Asn, Gln, Asp, Lys, Arg, Glu or His, and $aa_3$ is Ser, Val, or Asn (SEQ ID NO:28), or (b) $aa_1$ is Val or Leu, $aa_2$ is Asn and $aa_3$ is Ser, Val, or Asn (SEQ ID NO:29), or (c) $aa_1$ is Val or Leu, $aa_2$ is Gly, Ser, Thr, Cys, Tyr, Asn, Gln, Asp, Lys, Arg, Glu or His, and $aa_3$ is Ser or Asn (SEQ ID NO:30), wherein said proteinase cleaves said substrate at the peptide bond between Ala and $aa_3$.

2. The proteinase substrate of claim 1 wherein said polypeptide contains the amino acid sequence Val-Asn-Ala-Ser (SEQ ID NO:29).

3. The proteinase substrate of claim 1 wherein said polypeptide is covalently linked to each of a fluorescent moiety and a quenching moiety, said moieties being separated by said polypeptide.

4. The proteinase substrate of claim 1 wherein said polypeptide is labeled with a radioactive moiety.

5. A substrate for cleavage by a herpes virus proteinase, said substrate comprising: (a) a polypeptide consisting of not more than about 25 amino acids, said polypeptide containing an amino acid sequence:

$aa_1$-$aa_2$-Ala-$aa_3$ (SEQ ID NO:31), wherein $aa_1$ is Val or Leu, $aa_2$ is a polar amino acid, and $aa_3$ is Ser, Val, or Asn, wherein said proteinase cleaves said substrate at the peptide bond between Ala and $aa_3$, and (b) an indicator enzyme linked to said polypeptide, said polypeptide sterically inhibiting activity of said indicator enzyme, wherein upon cleavage by the proteinase between Ala and $aa_3$ the steric inhibition is relieved.

6. The substrate of claim 5 wherein a substrate for said indicator enzyme is linked to the polypeptide.

7. The substrate of claim 1 wherein the amino acid sequence contained in said peptide is within the indicator molecule.

8. The substrate of claim 7 wherein said indicator molecule is β-galactosidase or luciferase.

9. A substrate for cleavage by a herpes virus proteinase, said substrate comprising a polypeptide consisting of not more than about 25 amino acids, said polypeptide containing an amino acid sequence:

Tyr-$aa_4$-$aa_5$-Ala-$aa_6$ (SEQ ID NO:32), wherein $aa_4$ is Val or Leu, $aa_5$ is Lys or Gln, and $aa_6$ is Ser or Asn, wherein said proteinase cleaves said substrate at the peptide bond between Ala and $aa_6$, and wherein said polypeptide is optionally linked to a moiety selected from the group consisting of: a fluorescent moiety, a quenching moiety, a radioactive moiety, an enzyme, and an enzyme substrate.

10. The substrate of claim 9 wherein $aa_4$ is Leu, $aa_5$ is Lys or Gln and $aa_6$ is Ser (SEQ ID NO:32).

11. The substrate of claim 9 wherein said polypeptide contains the amino acid sequence Tyr-Val-Lys-Ala-Ser (SEQ ID NO:32).

12. The substrate of claim 9 wherein said polypeptide is covalently linked to each of a fluorescent moiety and a quenching moiety, said moieties being separated by said polypeptide.

13. The substrate of claim 9 wherein said polypeptide is labeled with a radioactive moiety.

14. A substrate for cleavage by a herpes virus proteinase, said substrate comprising: (a) a polypeptide consisting of not more than about 25 amino acids, said polypeptide containing an amino acid sequence:

Tyr-$aa_4$-$aa_5$-Ala-$aa_6$ (SEQ ID NO:33), wherein $aa_4$ is Val or Leu, $aa_5$ is Lys or Gln, and $aa_6$ is Ser or Asn, wherein said proteinase cleaves said substrate at the peptide bond between Ala and $aa_6$, and (b) an indicator enzyme linked to said polypeptide, said polypeptide sterically inhibiting activity of said indicator enzyme, wherein upon cleavage by said proteinase between Ala and $aa_6$ steric inhibition of activity is relieved.

15. The substrate of claim 14 wherein a substrate for said indicator enzyme is linked to the polypeptide.

16. The substrate of claim 9 wherein the amino acid sequence contained in said peptide is within the indicator molecule.

17. The substrate of claim 16 wherein said indicator molecule is β-galactosidase or luciferase.

18. An inhibitor of a herpes virus proteinase comprising a polypeptide derivative consisting of not more than about 25 amino acids, said polypeptide derivative containing an amino acid sequence:

$aa_1$-$aa_2$-Ala-$aa_3$ (SEQ ID NO:34), wherein $aa_1$ is Val or Leu, $aa_2$ is a polar amino acid, and $aa_3$ is Ser, Val, or Asn, wherein the bond between Ala and $aa_3$ is selected from the group consisting of a hydroxyethylamine linkage, a phosphonamide linkage, a carbon fluoride aldehyde, and a dialcohol linkage.

19. The inhibitor of claim 18 wherein the bond between Ala and $aa_3$ is a hydroxyethylamine linkage.

20. The inhibitor of claim 18 wherein the bond between Ala and $aa_3$ is a phosphonamide linkage.

21. The inhibitor of claim 18 wherein the bond between Ala and $aa_3$ is a carbon fluoride aldehyde.

22. The inhibitor of claim 18 wherein the bond between Ala and $aa_3$ is a dialcohol linkage.

23. An inhibitor of a herpes virus proteinase comprising a polypeptide derivative consisting of not more than about 25 amino acids, said polypeptide derivative containing an amino acid sequence:

Tyr-$aa_4$-$aa_5$-Ala-$aa_6$ (SEQ ID NO:35), wherein $aa_4$ is Val or Leu, $aa_5$ is Lys or Gln, and $aa_6$ is Ser or Asn, wherein the bond between Ala and $aa_6$ is selected from the group consisting of a hydroxyethylamine linkage, a phosphonamide linkage, a carbon fluoride aldehyde, and a dialcohol linkage.

24. The inhibitor of claim 23 wherein the bond between Ala and $aa_6$ is a hydroxyethylamine linkage.

25. The inhibitor of claim 23 wherein the bond between Ala and $aa_6$ is a phosphonamide linkage.

26. The inhibitor of claim 23 wherein the bond between Ala and $aa_6$ is a carbon fluoride aldehyde.

27. The inhibitor of claim 23 wherein the bond between Ala and $aa_6$ is a dialcohol linkage.

28. The substrate of claim 1 wherein said polypeptide consists of at least 15 amino acids.

29. The substrate of claim 9 wherein said polypeptide consists of at least 15 amino acids.

30. An inhibitor of herpes virus proteinase activity, said inhibitor comprising a polypeptide consisting of at least 6 and not more than about 12 L-isomer amino acids containing an amino acid sequence:

$aa_1$-$aa_2$-Ala-$aa_3$, wherein (a) $aa_1$ is Leu, $aa_2$ is Gly, Ser, Thr, Cys, Tyr, Asn, Gln, Asp, Lys, Arg, Glu or His, and $aa_3$ is Ser, Val, or Asn (SEQ ID NO:36), or (b) $aa_1$ is Val or Leu, $aa_2$ Asn and $aa_3$ is Ser, Val, or Asn (SEQ ID NO:37), or (c) $aa_1$ is Val or Leu, $aa_2$ is Gly, Ser, Thr, Cys, Tyr, Asn (SEQ ID NO:38), Gln, Asp, Lys, Arg, Glu or His, and $aa_3$ is Ser or Asn.

31. An inhibitor of herpes virus proteinase activity, said inhibitor comprising a polypeptide consisting of at least 6 and not more than about 12 amino acids containing an amino acid sequence:

Tyr-$aa_4$-$aa_5$-Ala-$aa_6$ (SEQ ID NO:35), wherein $aa_4$ is Val or Leu, $aa_5$ is Lys or Gln, and $aa_6$ is Ser or Asn.

* * * * *